(12) United States Patent
Ulmer (10) Patent No.: US 9,538,942 B2
(45) Date of Patent: Jan. 10, 2017

(54) MEDICAL SENSOR SYSTEM FOR DETECTING A FEATURE IN A BODY

(75) Inventor: Jens Ulmer, Zurich (CH)

(73) Assignee: BIOTRONIK SE & Co. KG (DE)

( * ) Notice: Subject to any disclaimer, the term of this patent is extended or adjusted under 35 U.S.C. 154(b) by 1497 days.

(21) Appl. No.: 13/226,522

(22) Filed: Sep. 7, 2011

(65) Prior Publication Data

US 2012/0078068 A1    Mar. 29, 2012

Related U.S. Application Data

(60) Provisional application No. 61/387,015, filed on Sep. 28, 2010.

(51) Int. Cl.
*A61B 5/145*   (2006.01)
*A61B 5/055*   (2006.01)
*A61B 5/00*    (2006.01)
*A61B 5/1473*  (2006.01)

(52) U.S. Cl.
CPC ......... *A61B 5/14532* (2013.01); *A61B 5/0031* (2013.01); *A61B 5/055* (2013.01); *A61B 5/14735* (2013.01); *A61B 5/6846* (2013.01); *A61B 5/681* (2013.01); *A61B 5/6898* (2013.01); *A61B 2560/0443* (2013.01); *A61B 2562/12* (2013.01)

(58) Field of Classification Search
CPC ..... A61B 5/1486; A61B 5/0031; A61B 5/055; A61B 5/14532; A61B 5/14735; A61B 5/6846
USPC ........................................ 600/302, 365, 347
See application file for complete search history.

(56) References Cited

U.S. PATENT DOCUMENTS

| | | | |
|---|---|---|---|
| 6,002,954 A | | 12/1999 | Van Antwerp |
| 6,110,660 A | * | 8/2000 | Kriz et al. ........................ 435/4 |
| 6,682,938 B1 | | 1/2004 | Satcher, Jr. et al. |
| 2010/0056894 A1 | * | 3/2010 | Cote et al. .................... 600/365 |
| 2011/0152713 A1 | | 6/2011 | Stephan et al. |

(Continued)

FOREIGN PATENT DOCUMENTS

WO    WO 2010/006592 A2    1/2010

OTHER PUBLICATIONS

Andrea Prieto Astalan et al.; "Biomolecular reactions studied using changes in Brownian rotation dynamics of magnetic particles", *Biosensors and Bioelectronics*, Elsevier BV, NL, Bd. 19, Nr. 8, 15. Mar. 2004, pp. 945-951, XP008130202, ISSN: 0956-5663, DOI: 10.1016/J.Bios.2003.09.005.

*Primary Examiner* — Navin Natnithithadha
*Assistant Examiner* — Eric Messersmith
(74) *Attorney, Agent, or Firm* — Craig A. Fieschko, Esq.; DeWitt Ross & Stevens S.C.

(57) ABSTRACT

The invention relates to a medical sensor system (10a/10c) for detecting a feature (12a/12c) in a human or animal body (14a/14c), including a signal pick-up unit (16a/16c), which can be implanted in the animal and/or human body (14a/14c), and a signal processing unit (18a/18c), which is spatially separated from the signal pick-up unit (16a/16c) and which includes a transmitter (20a/20c) and a receiver (22a/22c). The transmitter (20a/20c) emits an alternating magnetic field (24a/24c) to act on the signal pick-up unit (16a/16c), and the receiver (22a/22c) receives a response signal (26a/26c) of the signal pick-up unit (16a/16c), which is generated by the magnetic interaction of the alternating magnetic field (24a/24c) with the signal pick-up unit (16a/16c).

25 Claims, 7 Drawing Sheets

(56) References Cited

U.S. PATENT DOCUMENTS

2011/0275985 A1* 11/2011 Lowery, Jr. ........ A61B 5/14865
604/66
2011/0276124 A1* 11/2011 Doerr ........................ A61F 2/82
623/1.15

* cited by examiner

MEDICAL SENSOR SYSTEM FOR DETECTING A FEATURE IN A BODY

RELATED APPLICATION

This patent application claims the benefit of U.S. Provisional Patent Application No. 61/387,015, filed on Sep. 28, 2010, which is hereby incorporated by reference in its entirety.

FIELD OF THE INVENTION

The invention relates to a medical sensor system for detecting at least one feature in at least one human and/or animal body.

BACKGROUND OF THE INVENTION

In medicine, sensor systems are used wherein at least parts of the systems are inserted or implanted directly in a body of a patient in order to capture actual physiological conditions as precisely and directly as possible.

U.S. Pat. No. 6,682,938 B1 illustrates a sensor system based on an optical principle. A fluorescent dye within an injectable gel has fluorescence properties which change in dependence on an analyte concentration. The fluorescence change is read wirelessly by a signal processing system outside of the body. In order to obtain reliable measurement results, a complex calibration process is required. In addition, the system relies on direct contact of the sensor with a processing unit. As a result, components of the sensor or of the processing unit must be explanted after a certain period of time.

SUMMARY OF THE INVENTION

The invention seeks to provide a medical sensor system which has simple and reliable operation despite the use of a spatially separated sensor and processing unit. The medical sensor system allows detection of at least one feature in a human and/or animal body, and includes at least one signal pick-up unit that can be implanted in the body, and also includes at least one signal processing unit which includes a transmitter and a receiver, and which is spatially separated from the signal pick-up unit. The transmitter is designed to emit an alternating magnetic field to act on the signal pick-up unit, and the receiver is designed to receive a response signal of the signal pick-up unit, wherein the response signal is generated by the magnetic interaction of the alternating magnetic field with the signal pick-up unit.

Throughout this document, a "sensor system" shall be understood to refer to a system including at least one signal pick-up unit and at least one signal processing unit, which is used to detect a feature of a body (e.g., features of organs and/or tissue, in particular subcutaneous tissue). The term "feature" refers to a parameter, such as a pH value, a charge (for example of an ion), a temperature, a mass, a physical condition, a variable, and/or the absence, presence, and/or quantity of a substance, such as salt, sugar or protein, and/or an analyte. It is emphasized that other types of features are possible as well. The feature preferably relates to a variable component of the body.

A "signal pick-up unit" refers to a unit which responds to a state and/or a signal with a response signal wherein the response is dependent on the feature. The signal pick-up unit is formed of a biocompatible material, and is at least partially, and preferably completely, implanted in the body. Thus, the signal pick-up is disposed in vivo in a signal recording state. As an example, a signal processing unit may be defined by a passive biosensor.

A "signal processing unit" refers to a unit which measures, evaluates, and/or processes at least one response signal of the signal pick-up unit, and it preferably includes at least one receiver for this purpose. In addition, the signal processing unit includes a transmitter which is used to generate a signal in the form of an alternating magnetic field. An "alternating magnetic field" refers to a magnetic field having changing intensity and/or polarity, and which may be generated by alternating voltage or current. Furthermore, when it is stated that the alternating magnetic field "acts on the signal pick-up unit," this means that an interaction takes place between the alternating field and at least one component of the signal pick-up unit, thereby generating a response signal. The signal pick-up unit and the signal processing unit are disposed with spatial separation from each other, wherein "spatial separation" means that no physical connection exists between these units, and/or that the response signal of the signal pick-up unit can be read cordlessly or wirelessly by the signal processing unit. The signal processing unit is preferably designed as an AC susceptometer, and may output an assessment of a feature, for example to a patient or a physician, by way of a display unit using a processor.

The invention allows a measurement to be carried out in body tissue with advantageously low attenuation, which results in good, exact, and reliable measurement results. In addition, the need for complex calibration of the measurement system can be eliminated so as to save time and cost. Furthermore, the implantable signal pick-up unit can be smaller and less complex than previously known devices. Similarly, the form of the signal processing unit can also advantageously be reduced and more conveniently designed.

The medical sensor system may also include at least one magnetic nanoparticle which is designed to reversibly bind either to an analog of the analyte, or to a receptor of the analyte and the analog as a function of a concentration of an analyte. By implementing the functionalized magnetic nanoparticle and the analyte concentration-dependent reversible binding, a simple measurement principle can be employed, saving components and costs. The term "designed" shall be understood to mean specially provided, equipped, configured and/or prepared. Furthermore, a "magnetic nanoparticle" refers to a particle having a diameter and/or a major dimension between 1 nm and 100 nm, preferably between 10 nm and 50 nm, with 20 nm being particularly preferred. The nanoparticle includes a magnetic substance, such as compounds made of iron, nickel, cobalt, or chromium, and/or alloys made of manganese with aluminum, copper, tin, antimony, arsenic, bismuth, boron or other substances. However, other compounds and/or alloys are possible. The sensor system advantageously includes two or more nanoparticles, and advantageously has a mass concentration or a mass per sensor unit volume between 0.01 and 100 mg/ml, preferably between 0.1 and 50 mg/ml, with 1 to 10 m/gml being particularly preferred. A detectable mass concentration of 1 mg/ml, for example, corresponds to a particle count of 3.3 $10^{15}$, assuming a particle diameter of 20 nm. The magnetic nanoparticle may include $Fe_3O_4$ or be made of monodisperse iron oxide monocrystals, whereby it becomes particularly versatile and is biocompatible.

In addition, the nanoparticle may be functionalized by coating some, and preferably all, of its surface. The coating includes either a receptor of the analyte to be detected, or a receptor of an analog of the analyte to be detected. Binding of the functional molecules to the magnetic nanoparticles can be achieved, for example, by way of wet-chemical methods. The term "analyte" shall be understood to refer to the molecule or the substance which is to be detected in the body as a feature by the sensor system. Furthermore, the term "analog" refers to a molecule and/or a substance which is bound by the same receptor due to similar structure to the analyte, similar charge distribution, and/or another characteristic. The term "receptor" refers to a molecule and/or a substance which specifically binds the analyte and, given the similarity of the analog with the analyte, also binds the analog. The receptor may be a peptide, a protein (including antibodies and fragments thereof, RNA, or DNA), aptamers and the relatives thereof, cyclic macromolecules (including selectively binding ions or ionophores), non-cyclic macromolecules (including polymers having identifying features impressed during polymerization, i.e., molecular imprinted polymers), or other materials suitable for use as receptors. The term "reversible" refers to the ability to be reversed or detachable.

The signal pick-up unit includes the receptor where the particle is coated with the analog, and includes the analog where the particle is coated with the receptor. The receptor or analog are disposed on a fixed structure, such as a network or grid structure. The presence of these antagonists results in reversible binding between the analog and the receptor. The detection of the analyte is based on a displacement reaction, wherein the analyte displaces the analog from the receptor, or on competitive binding of the analyte and analog to the receptor. If the local concentration of the analyte in the analyzed tissue changes, the number of binding sites between the analog and the receptor is reduced, and the functionalized magnetic nanoparticle—which was initially fixed relative to the rigid structure due to the analog binding to the receptor/experiences a change of movement, rotation, and/or magnetic relaxation in relation to the rigid structure. This change can be measured using an alternating magnetic field having a magnetic flux density with an amplitude of 0.5 mT, for example.

The analyte is preferably a carbohydrate and/or a polysaccharide. However, any other substance (or family thereof) suitable for use as an analyte, such as peptides, hormones, proteins, fats, DNA, RNA, nucleotides, ions, pH and the like, can be used. The signal pick-up unit, however, is preferably designed as a sensor for a glucose analyte, whereby an actual concentration of glucose can be determined particularly quickly using a simple design.

Preferably, the receptor takes the form of one and/or more lectins chemically bound to the surface of the nanoparticle. As an alternative, carbohydrates and/or polysaccharides can be used. As a result, lectins, carbohydrates, and/or polysaccharides are disposed on the rigid structure as analogs.

The analog is preferably formed by a dextran, and/or the receptor can be formed by Concanavalin A, whereby the nanoparticle is coated with Concanavalin A. The converse of this arrangement can also be used. Owing to the pairing of dextran with Concanavalin A, the sensor system can be selectively adjusted to glucose as the analyte. Particularly robust glucose detection can be provided when glucose concentration influences a binding behavior of a magnetic nanoparticle coated with Concanavalin A to dextran, and thereby changes the relaxation behavior of the nanoparticle.

The signal pick-up unit may include at least one hydrogel formed by cross-linked dextran molecules, wherein "hydrogel" refers to a gel made of a polymer or copolymer which contains water, but is water-insoluble. Furthermore, the molecules thereof are linked chemically, such as by covalent or ionic bonds, or physically, such as by looping polymer chains, to form a three-dimensional network. The dextran molecules preferably have a weight between 1 kDa and 500 kDa, preferably between 10 kDa and 200 kDa, with 15 kDa to 25 kDa being particularly preferred. The hydrogel preferably has a consistency that allows it to be easily injected subcutaneously. The hydrogel is preferably administered under the skin, and is suspended in a solution suited for injection purposes as a dispersion of gel spherules measuring 200 to 300 μm. However, the hydrogel may gel in situ, for example due to a temperature change. The hydrogel allows the signal pick-up unit or the biosensor to be placed into the tissue particularly easily by way of injection. It is also patient-friendly and beneficial for the patient's health, insofar as few or no foreign body reactions occur after implantation. Furthermore, owing to lack of (or little) inflammation or other bodily reaction to foreign matter, there is little or no influence on the condition of the body at the implantation site, thereby creating optimal detection conditions.

The hydrogel is particularly advantageously formed by a copolymer, wherein "copolymer" refers to a polymer that contains different polymer types, for example, at least one other molecule building block in addition to dextran molecules, and which is cross-linked to a suitable degree. As a result, other properties in addition to the receptor property may be easily integrated into the hydrogel and/or the signal pick-up unit, such as increased biocompatibility, a better degradation rate, simplified injectability, and/or optimized ex vivo stability.

At least one magnetic nanoparticle is preferably disposed in the hydrogel, and the nanoparticle(s) are preferably homogeneously distributed over the hydrogel (though an inhomogeneous distribution is also possible). The nanoparticles can reversibly bind in particular to the hydrogel or structures of the hydrogel. Due to the arrangement of the nanoparticles—which are preferably coated with Concanavalin A—in the hydrogel, and preferably in a dextran copolymer hydrogel, the fixation of the nanoparticles by the receptor-analog interaction is particularly easily achieved.

Alternatively, where the nanoparticles have a dextran coating as the analog, the dextran can be partially or entirely omitted in the copolymer backbone. In contrast, the Concanavalin A receptor must be suitably chemically bound to the hydrogel.

The signal processing unit is disposed at a distance from, but in nearby vicinity to, the signal pick-up unit. It is preferably disposed sufficiently far away so as not to be implanted, whereby it is advantageously disposed ex vivo (outside of the body). The signal pick-up unit therefore does not require an internal power supply, thereby saving space and weight. Furthermore, the power required for the measurement can be supplied wirelessly by way of the externally applied alternating magnetic field.

The signal processing unit can be configured particularly conveniently when it is located in an external device such as a laptop or a mobile phone, or in an object or a commodity such as a piece of jewelry, a key ring, glasses, or preferably in a wrist watch. The signal processing unit can be configured particularly compactly when integrated in a wrist watch.

The signal pick-up unit is usefully at least partially surrounded by a biodegradable layer, most preferably at least 50% surrounded, and most preferably 100% surrounded. A signal pick-up unit including the aforementioned dextran hydrogel and the receptor-coated magnetic nanoparticles is preferably disposed in a core surrounded by the layer. The biodegradable layer is preferably composed of polymers including vinyl esters, acrylates, methacrylates, lactic acid, glycolic acid and/or other lactones, or N-isopropylamide. The polymer layer is preferably largely (more than 90%) or entirely permeable to the analyte. With this shell/core design of the signal pick-up unit, it can be ideally configured for analyte-receptor-analog binding, and for biocompatibility and/or biodegradability.

The signal pick-up unit preferably has complete biodegradability, whereby after it is no longer needed for feature detection, it does not have to be explanted. Its degradability, and in particular time-controlled proteolytic biodegradation of the hydrogel, can advantageously be further improved by using a copolymer which includes biodegradable polymer chains to which the dextran molecules having low molecular weight (20 kDa) are bound. These polymer chains can be composed of acrylates, methacrylates, vinyl esters, carbonates, caprolactones, lactic acid, glycolic acid and/or any other suitable molecule. Variable spacers may be incorporated in the polymer chain, for example such made of polyethylene glycol, polypropylene glycol, or the like. A polymerization process can be initiated, for example, using thermal or light-induced radical starters. With this composition, a degradation rate in the body can be adjusted by way of hydrophilic and hydrophobic properties of the spacers.

It is useful if the signal pick-up unit can degrade when subjected to an external stimulus, or if the biodegradability can be triggered from outside. Chemical stimuli, such as a change in pH value caused by supplying a weak acid or by causing an inflammatory reaction, can be used. Polymers, which, for example, are composed of acrylic acid, methacrylic acid, maleic anhydride, or N,N-dimethylaminoethylmethacrylate, respond with sensitivity to a pH change. This change brings about a change in the solubility of the polymer backbone, and accordingly in the degradability of the hydrogel.

The external stimulus preferably has a physical origin, such as a change in the temperature, whereby the stimulus can be easily generated. For this purpose, the hydrogel can incorporate a copolymer system in which thermoresponsive polymer units are bound to the low-molecular dextran units. The thermoresponsive units are preferably polymers which can be synthesized from monomers such as N-isopropylacrylamide, N,N-diethylacrylamide, methyl vinyl ether, N-vinylcaprolactam, and ethylene oxide-co-propylene oxide. These change the solubility properties of the copolymer in an aqueous medium as a function of the temperature, and can therefore specifically make the hydrogel susceptible to biodegradation. Furthermore, polymer units that control swelling behavior and biocompatibility can be incorporated, with examples being poly-lactic-glycolic acid, polyethylene glycol, polypropylene glycol, and polymers made of acrylates, methacrylates, and vinyl ester.

The signal pick-up unit is particularly advantageous when it includes at least one monomer from the group consisting of N-isopropylacrylamide, N,N-diethylacrylamide, methyl vinyl ether, N-vinylcaprolactam, ethylene oxide-co-propylene oxide, lactic acid, glycolic acid, trimethylcarbonate, acrylate, methacrylate, hydoxyethylene-methacrylate, and vinyl ester, whereby stimulation of temporal and thermal biodegradability can be easily achieved. Any combination of these monomers, with or without dextran, may be used.

Furthermore, biodegradability can be stimulated thermally by applying a strong alternating magnetic field. A "strong alternating magnetic field" should be understood to refer to a field which, over a period of less than 30 minutes, and most preferably less than at least 10 minutes, acts on the nanoparticles with a magnetic field strength H of less than 100 kA/m, preferably less than 50 kA/m, most preferably less than 20 kA/m and in particular 10 kA/m, at a frequency of 300-400 kHz. The nanoparticles convert the applied strong alternating magnetic field into heat, whereby the temperature change prompts the change in solubility described above.

As an example, at a field strength H of approximately 10 kA/m, a heating capacity of 100 W/g iron particles may be achieved. Since the thermoresponsive polymers undergo reversible conformation changes, an application time of 10 minutes is useful so that the collapse of the polymer backbone and the heating of the surrounding tissue lead to a mild inflammatory reaction in the body, which speeds up the degradation of the hydrogel. In addition, the temperature increase can deactivate the receptor, such as ConA, and reduce the binding ability to the analyte and/or the analog, or to dextran/glucose. In this way, a phase separation of the hydrogel components may take place, which in turn accelerates degradation. Because of this configuration, a separate device for stimulating degeneration need not be used because the signal processing unit can be used for this purpose, saving space, cost, components and installation space.

In another variation of the invention, a functionalized magnetic nanoparticle is provided for reversibly binding a hydrogel implanted in the body, and this binding determines a relaxation behavior of the nanoparticle in the alternating magnetic field. The term "functionalized" should be understood to mean modified and/or particularly advantageously coated. This allows the quantity of analyte to be determined particularly easily and reliably.

The invention extends to a method for reading a medical sensor system, wherein a transmitter of a signal processing unit emits an alternating magnetic field to act on a signal pick-up unit, and a receiver of the signal processing unit receives a response signal of the signal pick-up unit which is generated by the magnetic interaction of the alternating magnetic field with the signal pick-up unit.

Easy detection and measurement can be carried out when the response signal is formed by a relaxation signal of at least one nanoparticle. Measurement of the relaxation time can advantageously take place inherently and is independent of the applied energy. Furthermore, a simple reference system may be used. The relaxation signal is preferably caused by a change in the binding behavior between the nanoparticle(s) and a component of a hydrogel, wherein the binding behavior is independent of a concentration of an analyte. The change in the binding behavior can be determined by applying an external alternating magnetic field. If the nanoparticle is present in the unbound or free state, the complex susceptibility is higher (for example, having a maximum of 50 kHz) than that of a particle that is present in the bound or no longer free state (for example, having a maximum of 20 Hz). This difference is due to the fact that in free particles an isotropic reorientation of the particles takes place by way of Brownian relaxation after deactivating the magnetic field, while bound particles are subject to Neel relaxation. Because these are two different mechanisms, the time constants during which the isotropic reorientation occurs are also different (µs versus s). This significantly impacts the resonant frequency of the measurement. With the analyte concentration-dependent binding behavior, a mechanism can be provided which influences the relaxation signal in a directly proportional manner, whereby it is particularly easy to implement in terms of the design.

Advantageously, the signal pick-up unit becomes biodegradable after a predetermined amount of time by way of a thermally controlled signal, wherein the time can be controlled using a simple design by means of molecules that are incorporated in the hydrogel. The signal serves as a trigger for the degradation process, which may last several weeks. The signal pick-up unit and/or the hydrogel are preferably completely degrade within a period of less than one year, preferably less than half a year, most preferably less than 12 weeks and in particular in 6 to 8 weeks. In addition, the degradation signal preferably reduces the functionality of the signal pick-up unit (i.e., its susceptibility or other measurable indication of binding) to less than 5%.

The invention also involves systems which allow ion concentrations to be selectively detected in the subcutaneous tissue. Cryptands are attached to the hydrogel, and to the magnetic nanoparticle as receptor or analog. These bind the corresponding ion of the analyte only after two or more cryptand molecule units are combined. An example of this arrangement involves a potassium-selective sensor in which crown ethers are present both in the polymer matrix and on the magnetic nanoparticle. By way of 2:1 complexation (1 ion complexes with 2 crown ether rings), nanoparticles bind with the polymer backbone, which in turn impacts the relaxation behavior of the nanoparticles.

BRIEF DESCRIPTION OF THE DRAWINGS

Exemplary versions of the invention will be described below with reference to the drawings, wherein.

In the figures, functionally equivalent or equivalently acting elements are denoted with the same reference numerals. The figures are schematic illustrations of the invention, and do not depict specific parameters. In addition, the figures only reflect exemplary versions of the invention and are not intended to limit the invention to the versions that are illustrated. So as to avoid unnecessary repetitions, elements in a particular figure that are not described in detail below are provided with a reference to the respective description of the elements in the preceding figures.

DETAILED DESCRIPTION OF EXEMPLARY VERSIONS OF THE INVENTION

Figure 1A:
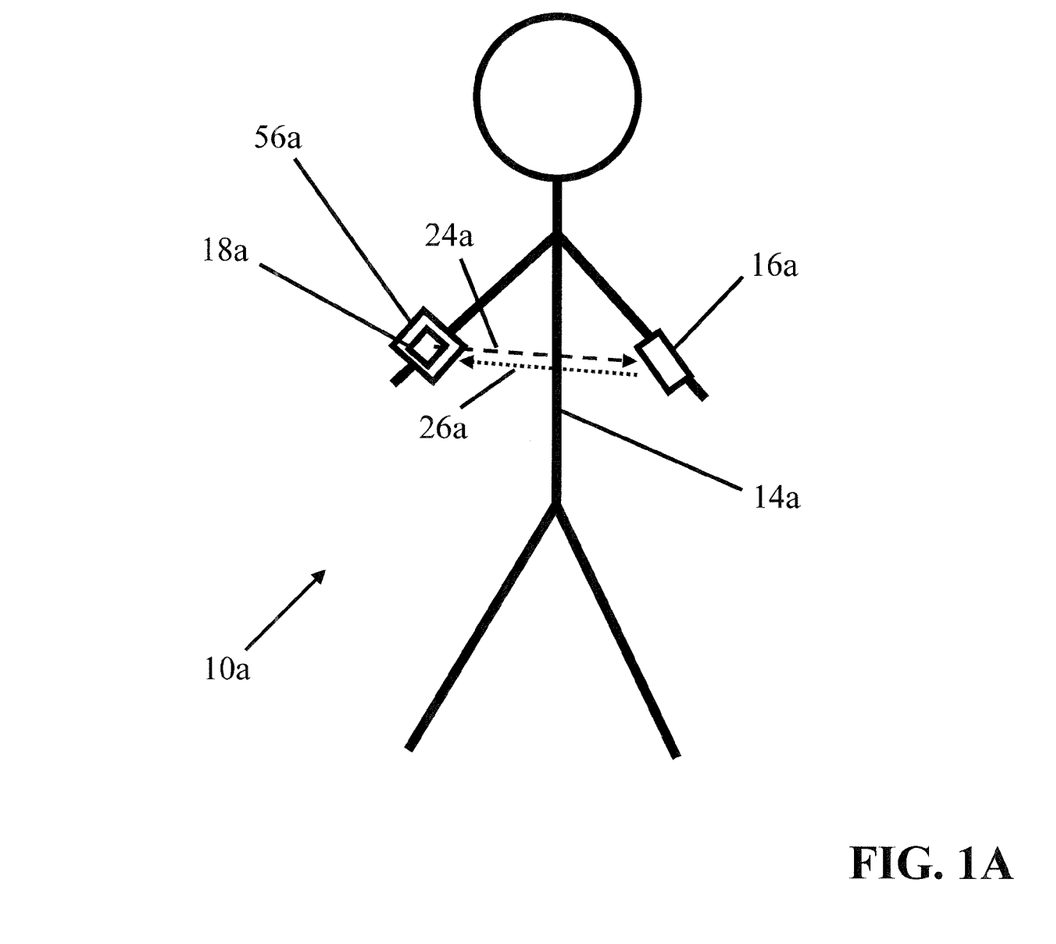
FIG. 1A shows a schematic illustration of a human wearing a partially implanted sensor system according to the invention.
Figure 1B:
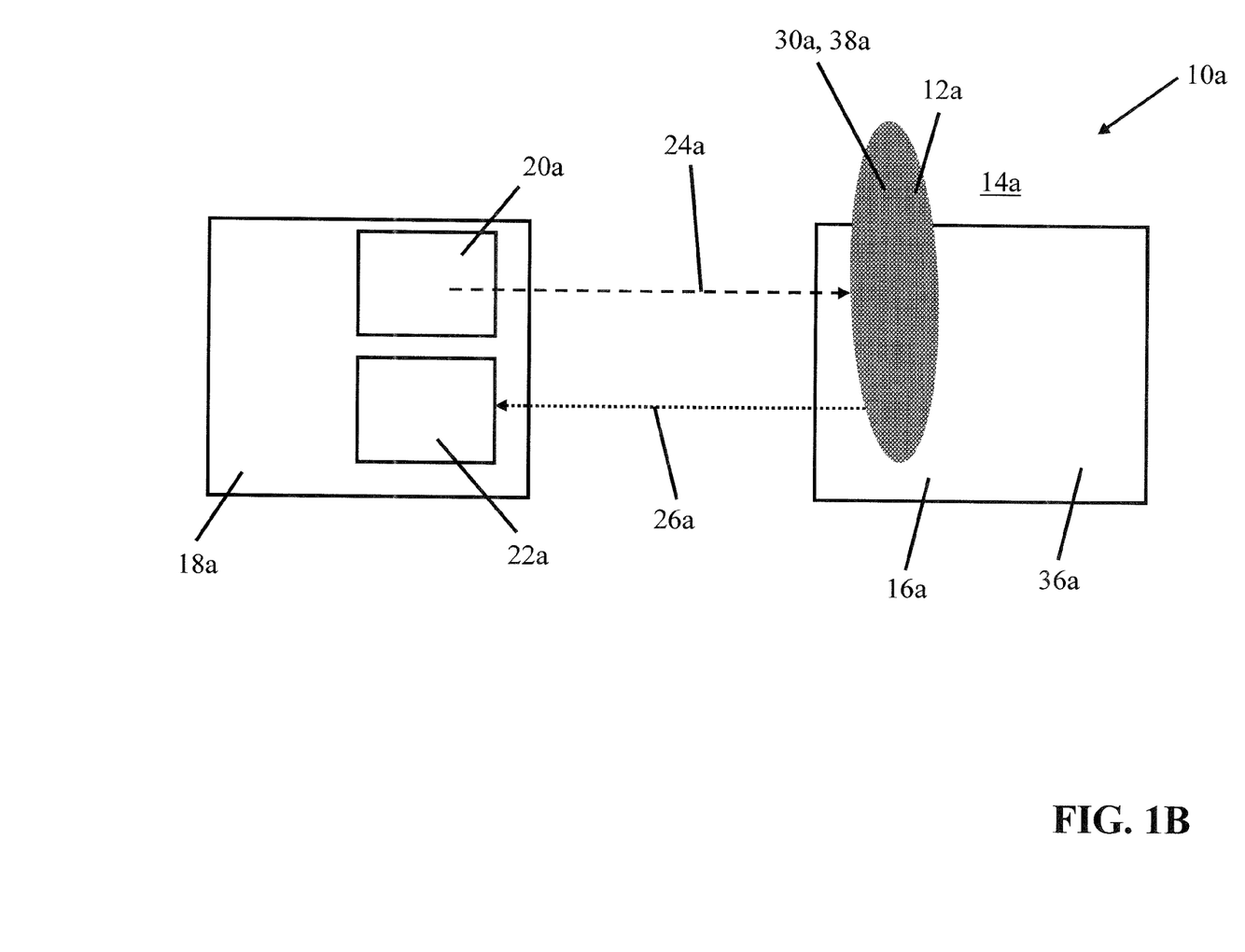
FIG. 1B shows a schematic detailed illustration of the sensor system of FIG. 1A.

FIG. 1A shows an exemplary medical sensor system 10a for detecting a feature 12a (FIG. 1B) in a human body 14a. Referring particularly to FIG. 1B, the feature 12a constitutes a quantity of an analyte 30a, for example, glucose 38a. As a result, the sensor system 10a is designed as a sensor 36a for glucose 38a. The sensor system 10a includes a signal pick-up unit 16a, which is implanted in the human body 14a in the subcutaneous tissue directly under the skin (at the forearm in FIG. 1A), and a signal processing unit 18a in the form of an AC susceptometer. The signal processing unit 18a is disposed outside the body in a wrist watch 56a, with spatial separation from the signal pick-up unit 16a. The signal processing unit 18a further includes a transmitter 20a and a receiver 22a, which are shown enlarged in FIG. 1B for better illustration.

The transmitter 20a is designed to emit an alternating magnetic field 24a having a magnetic flux density and an amplitude, for example, of 0.5 mT, to act on the signal pick-up unit 16a. The receiver 22a in turn is designed to receive a response signal 26a of the signal pick-up unit 16a. This response signal 26a is generated as a result of the magnetic interaction of the alternating magnetic field 24a with the signal pick-up unit 16a.

Figure 2A:
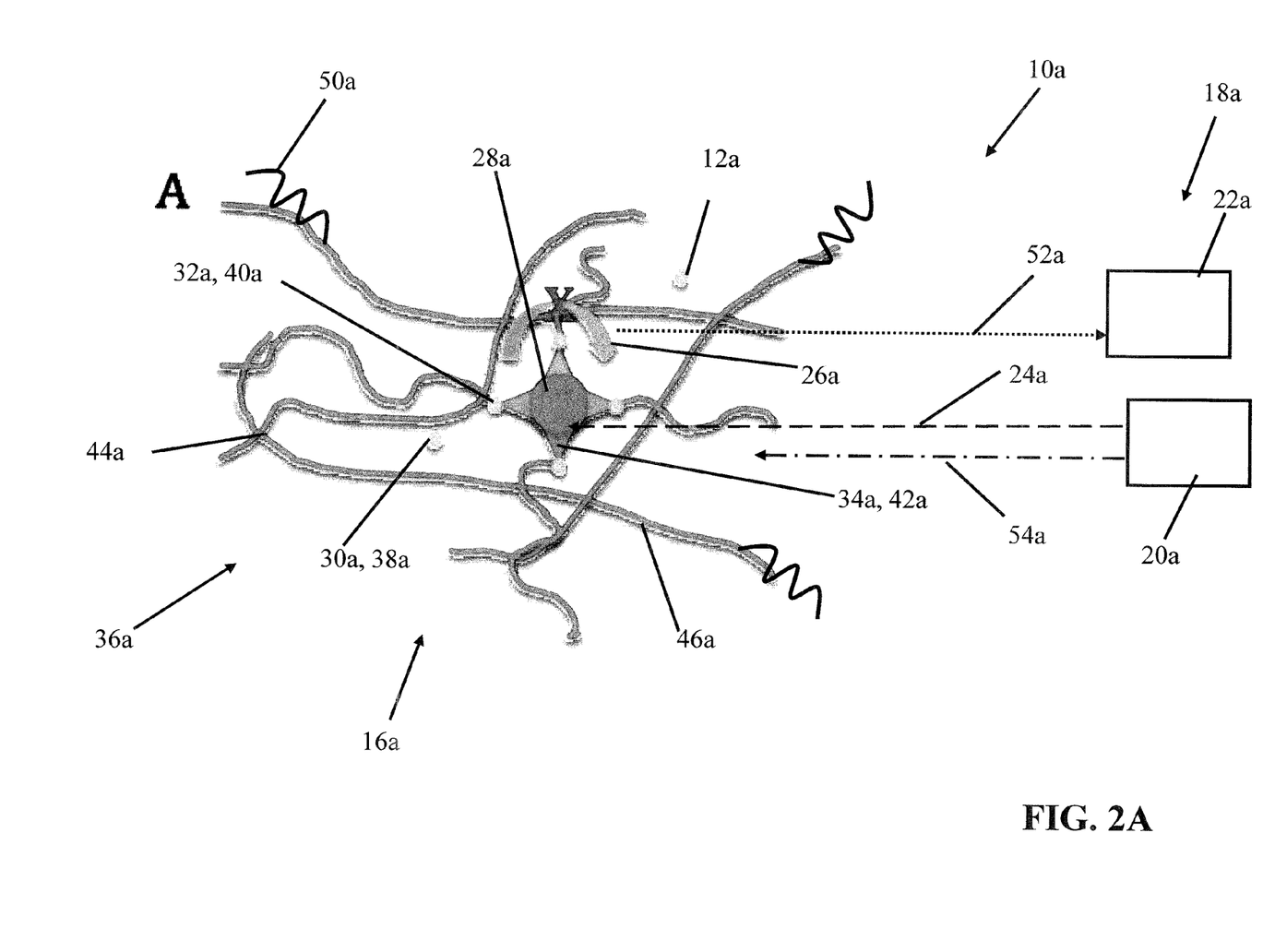
FIG. 2A is a schematic illustration of a nanoparticle embedded in a hydrogel for a low analyte concentration.

As seen in FIG. 2A, the signal pick-up unit 16a is provided for this purpose with magnetic nanoparticles 28a, e.g., made of $Fe_3O_4$ having a diameter of 20 nm, which are disposed or embedded in a hydrogel 44a. The hydrogel 44a may be composed of a dextran copolymer 46a, which in addition to the molecule chains made of dextran 40a includes polymers 50a made of a thermoresponsive component such as poly-N-isopropylacrylamide, as a result of which the thermoresponsive component can also be used directly as a cross-linker. Dextran molecule chains are shown wherein in certain cases the binding-relevant dextran molecules, or dextran molecules at the chain end in FIG. 2B, are illustrated as dots to provide a better understanding.

The nanoparticles 28a are functionalized in that they are coated with a receptor 34a of the analyte 30a. Here the receptor 34a is formed by the lectin Concanavalin A 42a. Given the similarity or agreement of glucose 38a with dextran 40a, the receptor 34a Concanavalin A 42a also binds to dextran 40a, whereby the dextran represents an analog 32a to the glucose analyte 30a. The coated nanoparticles 28a are therefore able to bind both to dextran 40a and thus to the hydrogel 44a, and to glucose 38a. This binding ability is reversible, whereby the binding state of the receptor 34a depends on the presence or absence (and consequently the concentration) of the analyte 30a.

Figure 2B:
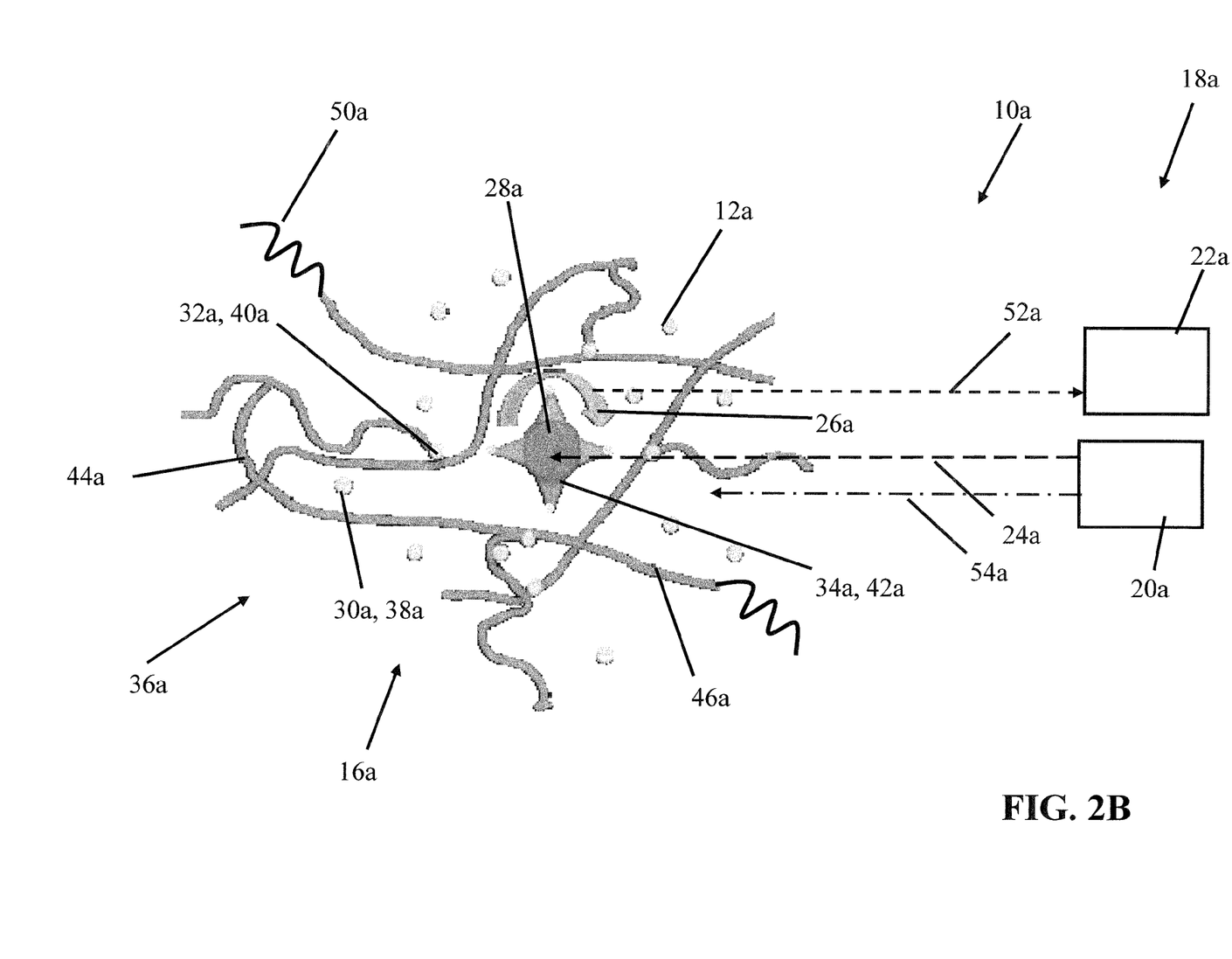
FIG. 2B is a schematic illustration of the nanoparticle of FIG. 2A for a high analyte concentration.

If the local concentration of glucose 38a changes or increases at the implantation site of the signal pick-up unit 16a, as is shown in FIG. 2B, the number of receptor 34a/analog 32a (or Concanavalin A 42a/dextran 40a) binding sites of the functionalized magnetic nanoparticles 28a to the polymer backbone of the hydrogel 44a is reduced by a competitive binding site of glucose 38a to Concanavalin A 42a. As a result, the rotational freedom of the now free nanoparticles 28a is increased. This can be measured via the alternating magnetic field 24a or the AC susceptometer. Because bound nanoparticles 28a are subject to Neel relaxation whereas free nanoparticles 28a are subject to the different mechanism of Brownian relaxation, the time constants during which the isotropic reorientation of the nanoparticles 28a occurs are also different (µs versus s). This results in considerably different (and measurable) resonant frequencies.

As a result, the concentration of glucose 38a influences the binding behavior of the magnetic nanoparticles 28a coated with Concanavalin A 42a to dextran 40a, and thereby changes the relaxation behavior of the nanoparticles 28a. The alternating magnetic field 24a thus generates a response signal 26a in the signal pick-up unit 16a in the form of a relaxation signal 52a, which is processed by the receiver 22a of the signal processing unit 18a into information about the amount of glucose 38a at the implantation site at the time of the measurement. This information could also be output by way of an output unit providing a visual, audible, or other detectable output.

Figure 3:
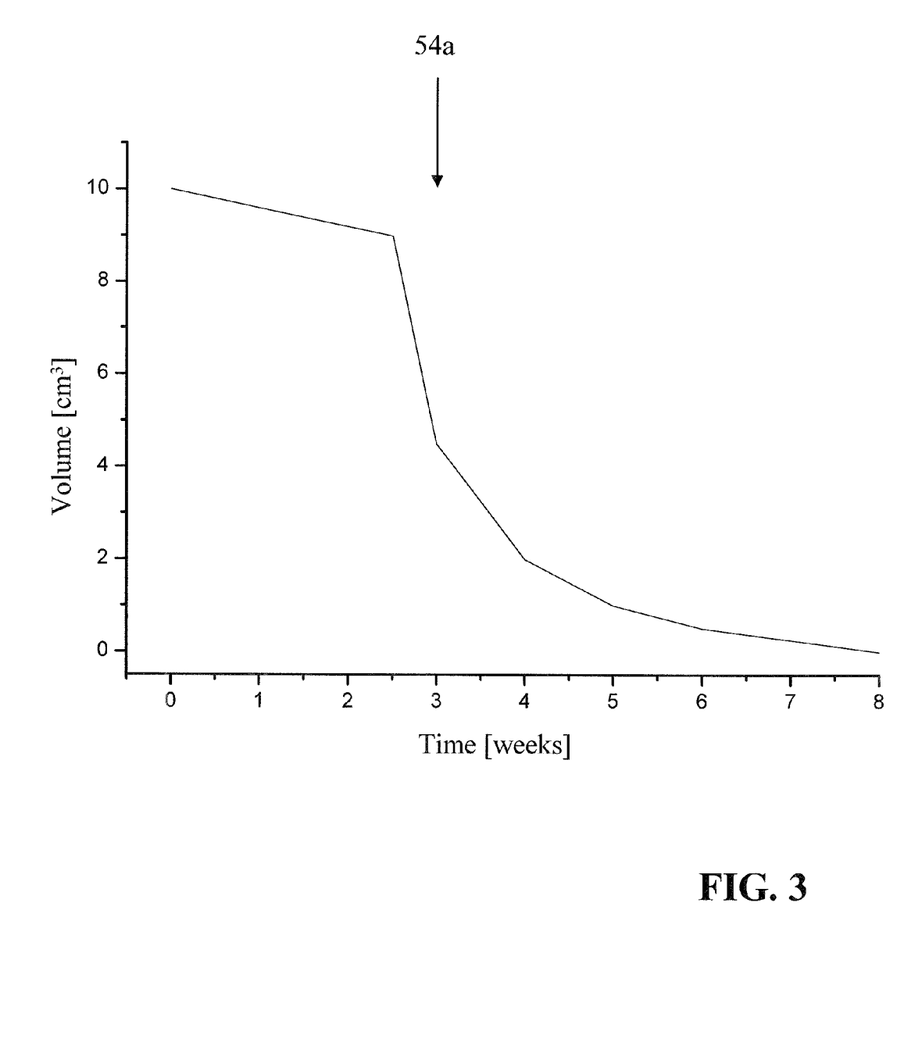
FIG. 3 is a degradation diagram of the signal pick-up unit of FIG. 1B.

With appropriate selection of the composition of the copolymer 46a of the hydrogel 44a or the polymer 50a, the implanted signal pick-up unit 16a can exhibit complete biodegradability. As illustrated in FIG. 3, this biodegradability can be stimulated by way of an external signal 54a after a certain usage period, for example three weeks after the sensor 36a was implanted. This signal 54a may be a thermal signal, which can be triggered by applying a strong alternating magnetic field 24a, for example of 10 kA/m, with a frequency of 350 kHz. This causes the magnetic nanoparticles 28a to convert the applied magnetic field into heat. Due to the temperature increase, a phase separation takes place and the hydrogel 44a shrinks and is subsequently completely degraded over a period of an additional five weeks due to a locally generated inflammatory reaction caused by the temperature increase. The loss of function of the signal pick-up unit 16a should take place immediately upon application of the external signal 54a, and the design described above makes it possible for the signal pick-up unit 16a to be rapidly degraded following its intended period of usage (and the loss of function thereof), without having to explant the unit 16a.

Figure 4:
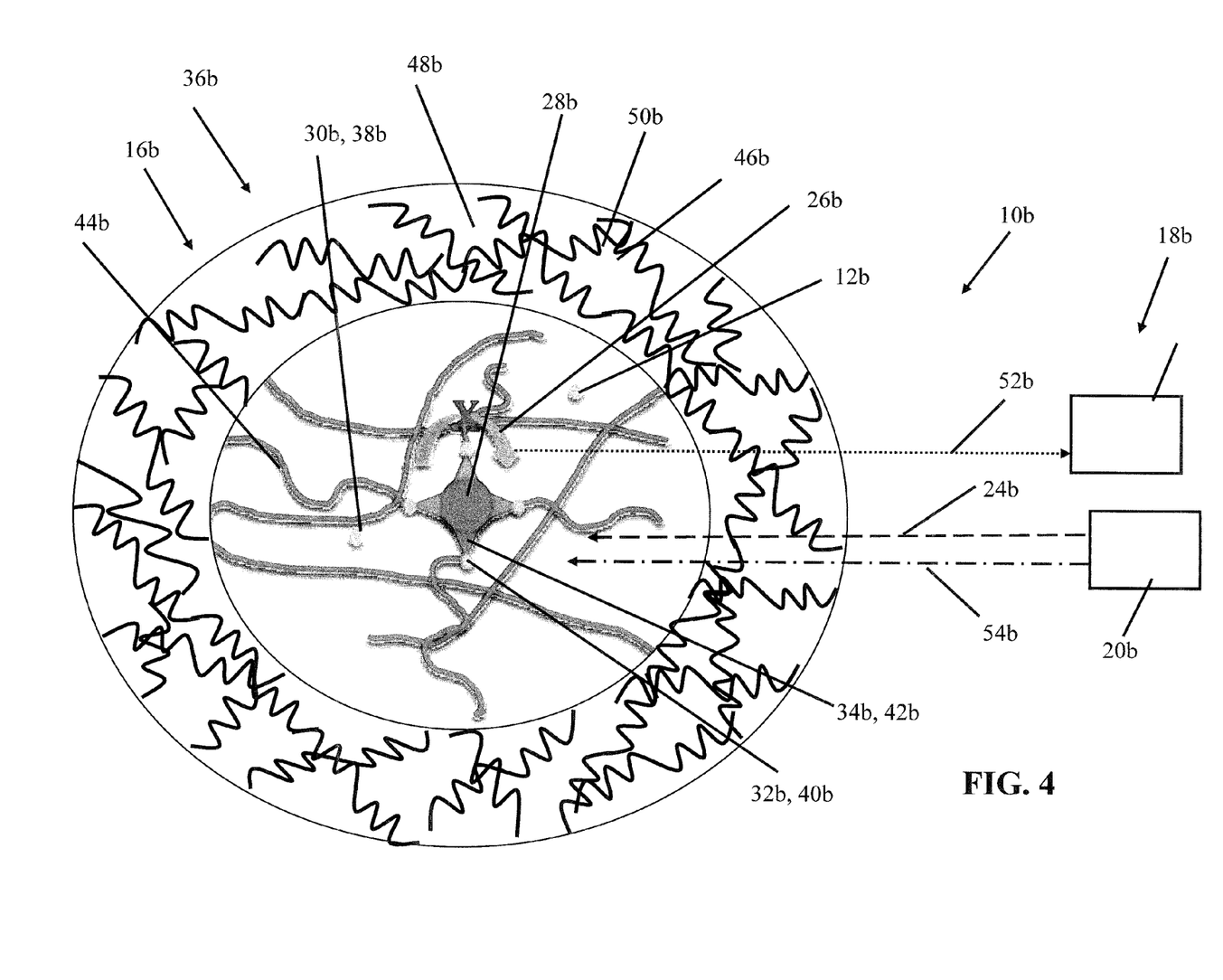
FIG. 4 is an alternative signal pick-up unit having a layer surrounding the signal pick-up unit.
Figure 5:
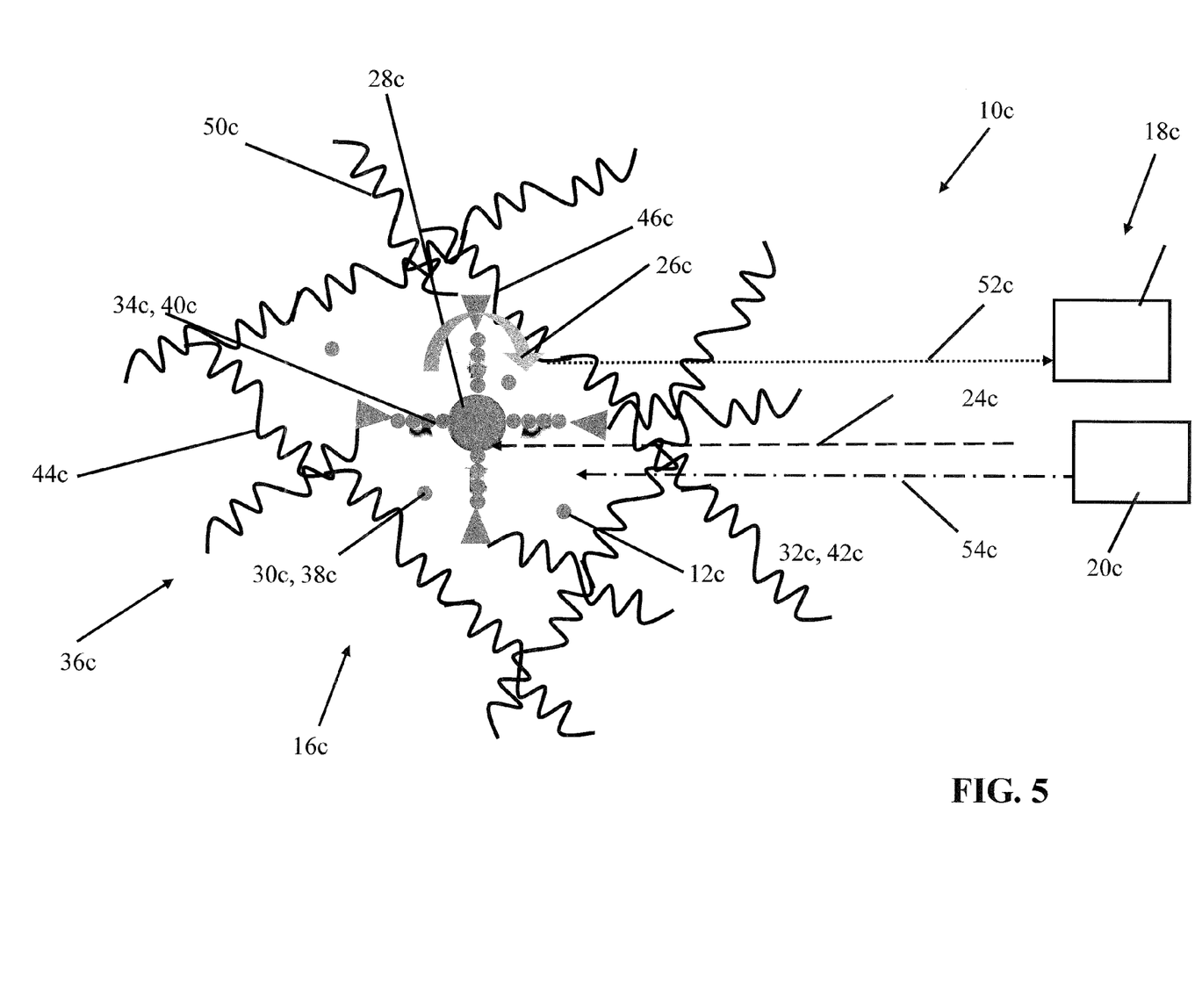
FIG. 5 is another alternative signal pick-up unit having a dextran-coated nanoparticle.

FIGS. 4 and 5 show alternative versions of the signal pick-up unit 16a. Components, features and functions similar to those above are marked with similar reference numerals, but the letters a to c have been added to the reference numerals to distinguish the versions. The description below focuses on the differences between these versions and the version of FIGS. 1 to 3, and thus the description of the version of FIGS. 1 to 3 should be referenced in regards to identical components, features, and functions.

FIG. 4 shows an alternative implantable signal pick-up unit 16b of a medical sensor system 10b for detecting a feature 12b in a human body (not shown in detail here). The signal pick-up unit 16b interacts with a signal processing unit 18b in a similar manner to that described in FIGS. 1 to 3, and is disposed outside the body with spatial separation from the signal processing unit 18b, and includes a transmitter 20b and a receiver 22b.

The signal pick-up unit 16b differs from the signal pick-up unit 16a of the first embodiment by being provided with a biodegradable layer 48b, which completely surrounds or encapsulates the signal pick-up unit 16b. The layer 48b is composed of a structure including a copolymer 46b with polymers 50b made of polyglycolic acid-co-lactic acid (PGLA) and poly-N-isopropylacrylamide (PNIPAAm). As a result of this design, the layer 48b is permeable to an analyte 30b in the form of glucose 38b. In addition, the layer 48b forms a shell around a core including a hydrogel 44b, which is formed by chains of the analog 32b dextran 40b and in which nanoparticles 28b are embedded, which are coated with the receptor 34b Concanavalin A 42b. The layer 48b is also biodegradable after a predetermined amount of time by way of a thermally controlled signal 54b.

FIG. 5 shows another alternative implantable signal pick-up unit 16c of a medical sensor system 10c for detecting a feature 12c in a human body (not shown in detail here). The signal pick-up unit 16c interacts with a signal processing unit 18c in a similar manner to that described in FIGS. 1 to 3, and is disposed outside the body with spatial separation from the signal processing unit 18c, and includes a transmitter 20c and a receiver 22c.

The signal pick-up unit 16c differs from the signal pick-up unit 16c of the first version discussed above by the inverted arrangement of a receptor 34c and an analog 32c of an analyte 30c. The signal pick-up unit 16c includes a hydrogel 44c, which is composed of a structure of copolymers 46c with polymers 50c, consisting of poly-hydroxyethyl-metacrylate, polyglycolic acid-co-lactic acid and poly-N-isopropylacrylamide components (polyHEMA-Co-PGLA and PNIPAAm), and in which nanoparticles 28c are embedded. These nanoparticles 28c are functionalized in that they include a coating made of dextran 40c as the analog 32c to the analyte 30c glucose 38c. In this version, the copolymer structure lacks dextran. However, a receptor 34c of the two analog/analyte molecules 38c, 40c in the form of Concanavalin-A 42c is chemically bound to the hydrogel 44c as an antagonist to glucose 38c, and to the dextran 40c bound to the nanoparticle 28c.

It will be apparent to those skilled in the art that numerous modifications and variations of the described examples and versions of the invention are possible in light of the foregoing discussion. The described examples and versions are presented for purposes of illustration only, and it is the intent to cover all such modifications and alternate versions that come within the scope of the claims below, or which are legally equivalent thereto.

What is claimed is:

1. A medical sensor system for detecting a feature in a body, the system including:
   a. a signal pick-up unit configured to be implanted within the body, the signal pick-up unit including:
      (1) a magnetic nanoparticle having a coating consisting essentially of a receptor, the receptor being configured to competitively bind to:
         (a) an analyte, and
         (b) an analog of the analyte,
         as a function of a concentration of the analyte;
      (2) at least one polymer of monomers from:
         (a) N-isopropylacrylamide,
         (b) N,N-diethylacrylamide,
         (c) methyl vinyl ether,
         (d) N-vinylcaprolactam,
         (e) ethylene oxide-co-propylene oxide,
         (f) lactic acid,
         (g) glycolic acid,
         (h) trimethylcarbonate,
         (i) acrylate,
         (j) methacrylate,
         (k) hydroxyethyl-metacrylate,
         (l) vinyl ester;
   b. a signal processing unit:
      (1) spatially separated from the signal pick-up unit, and
      (2) including:
         (a) a transmitter configured to emit an alternating magnetic field which acts on the signal pick-up unit to generate a response signal from the signal pick-up unit, and
         (b) a receiver configured to receive the response signal of the signal pick-up unit.

2. The medical sensor system of claim 1 wherein the signal pick-up unit is configured to generate a response signal dependent on the concentration of a glucose analyte.

3. The medical sensor system of claim 2 wherein the analog includes dextran.

4. The medical sensor system of claim 2 wherein the receptor includes Concanavalin A.

5. The medical sensor system of claim 1 wherein the receptor includes Concanavalin A.

6. The medical sensor system of claim 1 wherein the analog is at least partially formed of a hydrogel wherein the magnetic nanoparticle is disposed.

7. The medical sensor system of claim 6 wherein:
a. the magnetic nanoparticle, and
b. the analog,
are at least partially surrounded by a biodegradable layer.

8. The medical sensor system of claim 1 wherein the analog is configured to degrade upon application of an alternating magnetic field to the signal pick-up unit.

9. The medical sensor system of claim 7 wherein biodegradability is thermally activated.

10. The medical sensor system of claim 7 wherein biodegradability is activated by application of an alternating magnetic field.

11. The medical sensor system of claim 1 wherein the analog is at least partially formed of a hydrogel.

12. A method for detecting an analyte in a body using a sensor system, the system including:
A. a signal pick-up unit configured to be implanted within the body, the signal pick-up unit including:
  I. a magnetic nanoparticle,
  II. a hydrogel, the hydrogel including an analog of the analyte, and
  III. a coating on the nanoparticle, the coating consisting essentially of a receptor of the analyte and analog,
B. a signal processing unit spatially separated from the signal pick-up unit, the signal processing unit including a transmitter and a receiver;
wherein the method includes the steps of:
a. transmitting an alternating magnetic field from the transmitter, the magnetic field acting on the signal pick-up unit to generate a response signal therefrom;
b. receiving the response signal of the signal pick-up unit at the receiver.

13. The method of claim 12 wherein the signal processing unit is situated outside the body.

14. The method of claim 12 wherein the magnetic nanoparticle is configured to exhibit a magnetic susceptibility as the response signal, the susceptibility being dependent on the concentration of an analyte within the body.

15. The method of claim 12 further including the step of supplying an alternating magnetic field to the signal pick-up unit, the magnetic field being configured to induce biodegradation of the signal pick-up unit.

16. A medical sensor system for detecting an analyte in a body, the system including:
a. a signal pick-up unit configured to be implanted within the body, the signal pick-up unit including
  (1) a hydrogel, and
  (2) a magnetic nanoparticle being configured to exhibit a magnetic property dependent on the concentration of the analyte within the body,
  (3) a coating on the magnetic nanoparticle, the coating consisting essentially of a receptor of:
    (a) an analyte, and
    (b) an analog of the analyte,
    whereby the magnetic nanoparticle may reversibly bind to the analyte and analog via the receptor;
b. a signal processing unit:
  (1) situated outside the body, and
  (2) including:
    (a) a transmitter configured to emit an alternating magnetic field, and
    (b) a receiver configured to receive a response signal from at least the magnetic nanoparticle of the signal pick-up unit, the response signal being induced by the alternating magnetic field.

17. The medical sensor system of claim 16 wherein the magnetic nanoparticle is configured to bind to at least one of:
a. the hydrogel, and
b. the analyte,
in dependence on the concentration of the analyte within the body.

18. The medical sensor system of claim 12 wherein the hydrogel includes at least one polymer of monomers from:
a. N-isopropylacrylamide,
b. N,N-diethylacrylamide,
c. methyl vinyl ether,
d. N-vinylcaprolactam,
e. ethylene oxide-co-propylene oxide,
f. lactic acid,
g. glycolic acid,
h. trimethylcarbonate,
i. acrylate,
j. methacrylate,
k. hydroxyethyl-metacrylate,
l. vinyl ester.

19. The medical sensor system of claim 16 wherein the hydrogel is at least partially formed of the analog.

20. The medical sensor system of claim 19 wherein the hydrogel includes at least one polymer of monomers from:
a. N-isopropylacrylamide,
b. N,N-diethylacrylamide,
c. methyl vinyl ether,
d. N-vinylcaprolactam,
e. ethylene oxide-co-propylene oxide,
f. lactic acid,
g. glycolic acid,
h. trimethylcarbonate,
i. acrylate,
j. methacrylate,
k. hydroxyethyl-metacrylate,
l. vinyl ester.

21. The medical sensor system of claim 16 wherein the receptor includes Concanavalin A therein.

22. The medical sensor system of claim 16 wherein the signal pick-up unit is configured to biodegrade when an alternating magnetic field is supplied thereto.

23. The medical sensor system of claim 6 wherein the receptor is configured to release from the analog, and thus from the hydrogel, in the presence of the analyte.

24. The method of claim 12 wherein the receptor is configured to preferentially bind to the analyte, whereby the nanoparticle and the receptor thereon release from the analog of the hydrogel in the presence of the analyte.

25. The method of claim 16 wherein:
a. the hydrogel bears the analog thereon, and
b. the receptor is configured to preferentially bind to the analyte,
whereby the nanoparticle and the receptor thereon release from the analog of the hydrogel in the presence of the analyte.

* * * * *